United States Patent [19]
Fuchs

[11] Patent Number: 5,483,697
[45] Date of Patent: Jan. 16, 1996

[54] MULTILAYER PROTECTIVE COVERINGS WITH A SEALING SOLUTION

[75] Inventor: Ingbert E. Fuchs, Desoto, Tex.

[73] Assignee: Board of Regents The University of Texas, Austin, Tex.

[21] Appl. No.: 129,110

[22] PCT Filed: Nov. 27, 1991

[86] PCT No.: PCT/US91/08961

§ 371 Date: Oct. 1, 1993

§ 102(e) Date: Oct. 1, 1993

Related U.S. Application Data

[63] Continuation-in-part of Ser. No. 678,838, Apr. 1, 1991, which is a continuation-in-part of Ser. No. 422,913, Oct. 17, 1989, abandoned, which is a continuation-in-part of Ser. No. 359,474, May 22, 1989, abandoned.

[51] Int. Cl.$^6$ .............................. A41D 13/10; A61F 6/04
[52] U.S. Cl. ...................... 2/161.7; 2/168; 2/21; 128/844
[58] Field of Search ........................... 2/161.7, 167, 168, 2/169, 21, 901, 159, 161.6; 128/842, 844, 917, 918; 604/346, 347, 349; 428/916, 137, 138, 492, 493, 35.2, 520, 521, 494; 424/402, 404, 405, 443

[56] References Cited

U.S. PATENT DOCUMENTS

| 1,954,262 | 4/1934 | Potter . |
| 2,120,406 | 6/1938 | Hansen . |

(List continued on next page.)

FOREIGN PATENT DOCUMENTS

| 1917699 | 4/1969 | Denmark . |
| 0089181 | 9/1983 | European Pat. Off. . |
| 0089780 | 9/1983 | European Pat. Off. . |
| 0178856 | 4/1986 | European Pat. Off. . |
| 0299802 | 1/1989 | European Pat. Off. . |
| 0300814 | 1/1989 | European Pat. Off. . |
| 0328421 | 2/1989 | European Pat. Off. . |
| 0306389 | 3/1989 | European Pat. Off. . |
| 0411732 | 2/1991 | European Pat. Off. . |
| 2616062 | 12/1988 | France . |
| 61-9448 | of 0000 | Japan . |
| 61-14242 | of 0000 | Japan . |
| 61-152449 | of 0000 | Japan . |
| 540241 | 4/1942 | United Kingdom . |
| 2208358 | 3/1989 | United Kingdom . |
| 326719 | 6/1989 | United Kingdom . |
| WO83/00011 | 1/1983 | WIPO . |
| WO86/00908 | 3/1984 | WIPO . |
| WO84/02138 | 6/1984 | WIPO . |
| WO86/05391 | 9/1986 | WIPO . |
| WO90/14048 | 11/1990 | WIPO . |

OTHER PUBLICATIONS

*Plastics Fabrication and Uses*, vol. 74, No. 13928m (1971).
*Chemical Abstracts*, vol. 78, No. 31154t (1973).
*Webster's Third New International Dictionary*, at pp. 706–710 (1986).
"Standard Specification for Rubber Surgical Gloves," D3577–78, pp. 477–485, American Society for Testing and Materials (Jul. 1978).
"Standard Specification for Rubber Finger Cots," D3772–86, pp. 523–525, American Society for Testing and Materials (May 1986).
Hickes et al., "Inactivation of HTLV–III/LAV–Infected Cultures of Normal Human Lymphocytes by Moonoxynol–9 In Vitro," *The Lancet*, pp. 1422–1423 (Dec 21/28, 1985).
Grossgebauer, "Virus Disinfection," *Disinfection*, pp. 103–148 (1970).

(List continued on next page.)

*Primary Examiner*—C. D. Crowder
*Assistant Examiner*—Amy B. Vanatta
*Attorney, Agent, or Firm*—Arnold White & Durkee

[57] ABSTRACT

Protective covering such as a surgical glove, finger cot or condom having two layers with a middle layer of sealing solution disposed between the two layers. The solution operates to fill punctures or tears in the two layers. The middle layer may include an evaporation inhibitor to inhibit evaporation of antimicrobial or sealing solutions in the middle layer.

85 Claims, 7 Drawing Sheets

U.S. PATENT DOCUMENTS

| | | |
|---|---|---|
| 2,148,832 | 2/1939 | Raynolds . |
| 2,281,436 | 4/1942 | Hershberger . |
| 2,410,460 | 11/1946 | Robinson . |
| 2,586,674 | 2/1952 | Lönne . |
| 2,792,835 | 5/1957 | Ferguson . |
| 2,983,705 | 5/1961 | Baldwin et al. . |
| 2,983,707 | 5/1961 | Baldwin et al. . |
| 3,110,035 | 11/1963 | LaHue . |
| 3,121,877 | 2/1964 | Gintner . |
| 3,342,182 | 9/1967 | Charos . |
| 3,536,576 | 10/1970 | Schwartz . |
| 3,633,216 | 1/1972 | Schonholtz . |
| 3,672,351 | 6/1972 | Ubersax et al. . |
| 3,813,695 | 6/1974 | Podell, Jr. et al. . |
| 3,854,228 | 12/1974 | Conroy . |
| 3,874,000 | 4/1975 | Altman . |
| 3,883,899 | 5/1975 | Ganz . |
| 3,898,253 | 8/1975 | Buckler et al. . |
| 3,911,501 | 10/1975 | Seltzer . |
| 3,975,775 | 8/1976 | Alsop . |
| 4,070,713 | 1/1978 | Stockum . |
| 4,143,423 | 3/1979 | Sternlieb . |
| 4,185,330 | 1/1980 | Stager . |
| 4,190,040 | 2/1980 | Schulte . |
| 4,214,321 | 7/1980 | Nuwayser . |
| 4,218,779 | 8/1980 | Hart et al. . |
| 4,332,243 | 6/1982 | Gutnick . |
| 4,432,357 | 2/1984 | Pomeranz . |
| 4,442,147 | 4/1984 | Schirmer . |
| 4,446,860 | 5/1984 | Gutnick . |
| 4,471,538 | 9/1984 | Pomeranz et al. . |
| 4,482,577 | 11/1984 | Goldstein et al. . |
| 4,486,562 | 12/1984 | Fischer . |
| 4,499,154 | 2/1985 | James et al. . |
| 4,548,844 | 10/1985 | Podell et al. . |
| 4,575,476 | 3/1986 | Podell et al. . |
| 4,588,646 | 5/1986 | Athey, Jr. . |
| 4,597,108 | 7/1986 | Momose . |
| 4,657,021 | 4/1987 | Perry et al. . |
| 4,668,224 | 5/1987 | Lentz et al. . |
| 4,696,065 | 9/1987 | Elenteny . |
| 4,742,578 | 5/1988 | Seid . |
| 4,771,482 | 9/1988 | Shlenker . |
| 4,795,425 | 1/1989 | Pugh . |
| 4,843,014 | 7/1989 | Cukier . |
| 4,864,661 | 9/1989 | Gimbel . |
| 4,881,277 | 11/1989 | Hogle . |
| 4,892,779 | 1/1990 | Leatherman et al. . |
| 4,919,966 | 4/1990 | Shylenker . |
| 4,930,522 | 6/1990 | Busnel et al. . |
| 4,977,903 | 12/1990 | Haines . |
| 5,024,852 | 6/1991 | Busnel et al. . |
| 5,045,341 | 9/1991 | Shlenker . |

OTHER PUBLICATIONS

Rabinovich, et al., "Direct Measurements of Long–Range Surface Forces in Gas and Liquid Media," *Advances in Colloid and Interface Science*, vol. 16, pp. 63–78 (1982).

Rigel et al., "Modification of Surgical Gloves Prevent Exposure to Hepatitis During Hair Transplantation Surgery," *J. Dermaol. Surg. Oncol.*, 9:2, pp. 114–115 (Feb. 1983).

Spire et al., "Inactivation of Lymphadenopathy Associated Virus by Chemical Disinfectants," *The Lancet*, pp. 899–901 (Oct. 20, 1984).

Wright et al., "Mechanisms of Glove Tears and Sharp Injuries Among Surgical Personnel," *JAMA*, vol. 266, No. 12, pp. 1668–1671 (Sep. 25, 1991).

International Search Report for PCT/US90/02903 Application (Apr. 10, 1990).

International Search Report for PCT/US91/08623 Application (May 21, 1992).

International Search Report for PCT/US91/08961 Application (Jun. 12, 1992).

International Search Report for PCT/US91/08954 Application (May 19, 1992).

World Patents Index Latest, Derwent Ltd., London, GB; AN 81–90479D & SU,A,761 513, Abstract (Sep. 7, 1980).

*Nuclear Technology*, vol. 80, No. 127274z (1974).

Annex to the International Search Report of the International Patent Application No. 9002903.

Annex to the International Search Report on International Patent Application No. 91/08623.

Annex to the International Search Report on International Patent Application No. 91/08954.

Dialog Search Report No. 206405.

PCT Written Opinion No. 90/02903.

MULTILAYER PROTECTIVE COVERINGS WITH A SEALING SOLUTION

This is a continuation-in-part of application Ser. No. 678,838 filed Apr. 1, 1991, which is a continuation-in-part of Ser. No. 422,913 filed on Oct. 17, 1989 (now abandoned), which is a continuation-in-part of Ser. No. 359,474 filed on May 22, 1989 (now abandoned).

This invention relates to protective coverings (e.g., gloves, condoms, and finger cots) for human body members, and methods for making such protective coverings. More particularly, this invention relates to coverings such as protective gloves which may be used for various purposes, including, for example, surgery or other medical procedures, or protection from hazardous chemical substances.

The design of protective gloves represents a struggle of competing interests. To increase the protective nature of the glove intuitively requires increasing the thickness of the glove material. However, by increasing the thickness of the glove material, the sense of feel for the wearer of the gloves is increasingly hampered. Thus, the glove designer must find a suitable compromise between safety and sense of feel.

This problem is particularly acute in the area of surgical gloves. The sense of feel in the hands of a surgeon is important for the proper handling of delicate instruments and the proper execution of precise surgical procedures. However, it is also desirable that the surgeon be protected from biohazardous agents which the surgeon may be exposed to from the patient. For example, the surgical patient may carry viruses such as HIV (Human Immunodeficiency Virus) or hepatitis. During surgery, the surgeon's gloves are frequently cut or punctured, exposing the surgeon to infection.

Also, it is desirable to protect the patient from germs on the surgeon's or technician's hands. Although medical personnel, of course, typically scrub their hands before performing surgical procedures, some germs may remain and be exposed to the patient upon puncturing or tearing the surgical gloves.

Surgical gloves known to the Applicant are generally made of latex, vinyl, or neoprene, i.e. thin elastic materials which provide reasonable tear resistance and allow for satisfactory sense of feel. However, the gloves may be easily torn or punctured with sharp surgical instruments. Furthermore, it is difficult for the surgeon to detect a small tear or puncture in the glove material during surgery since such a puncture is difficult to see, especially if the gloves are covered with a patient's body fluids. Thus, the surgeon has little warning of exposure.

In the chemical or hazardous material preparation and handling area, disadvantages in present gloves also exist. Although the sense of feel for these areas may not be as important as that for the surgeon, there is also often a risk or danger even with thicker protective gloves. The glove material may be degraded or penetrated after a period of time by various chemicals which the chemist handles.

Protective coverings for other parts of the body also exist. For example, finger cots (i.e. glove-like coverings which cover only one finger) are used in medical procedures, particularly in rectal and vaginal examinations. Condoms are used to cover the male reproductive organ during intercourse. In addition to the obvious purpose of a condom to trap semen and thereby minimize the possibility of pregnancy resulting from intercourse, condoms are also used to protect the partners from infections by sexually transmitted diseases. This has become increasingly important over recent years in preventing the spread of HIV.

In these and other protective coverings, similar problems and concerns exist, i.e. danger of tearing or ripping the covering balanced against the desire for sensitivity.

Thus it is a general object of this invention to provide protective coverings which address the disadvantages experienced by the above-described coverings.

In one broad aspect, the present invention provides a protective covering for a human body member, the protective covering having an inner and outer layer. A layer of solution is disposed between the inner and outer layers, and an impermeable seal is provided between the layers to contain the solution substance therebetween. The solution may comprise an antimicrobial solution, a sealing solution, an evaporation inhibitor, a neutralizing solution, or any mixture thereof. The solution layer is generally less than about 0.12 millimeter ("mm") average thickness. Preferably the solution layer is thick enough such that capillary forces are exerted on the two covering layers, thereby providing a mechanical-like coupling between the two covering layers.

The term "protective covering" is used to mean any covering used to protectively cover a human body member. The term "human body member" is used broadly to include all limbs and external protrusions of the human body, e.g., fingers, hands, arms, toes, feet, legs, head, penis, etc. In many situations, a human body member may be exposed to biohazardous substances such as infected body fluids, or hazardous chemicals. Coverings are often used to protect body members from exposure to hazardous substances. Thus, the term "protective covering" includes such items as gloves, finger cots, condoms, boots and the like.

In a preferred embodiment, the present invention provides a surgical glove having an inner and outer layer. A layer of antimicrobial solution is disposed between the inner and outer layers, and an impermeable seal between the layers is provided. As stated above, the solution layer is generally less than about 0.12 mm in average thickness to provide a mechanical-like capillary coupling between the glove layers.

To maximize the capillary force exerted by the liquid layer, the average thickness of such layer is preferably between about 0.01 and 0.09 mm, most preferably between about 0.025 and 0.05 mm. Further, the liquid layer is preferably of substantially uniform thickness.

The term "antimicrobial solution" means herein a solution, typically aqueous, capable of killing or inactivating infectious agents, such as bacteria, virus, or microbes. Thus, the term includes, for example, virucides, bactericides, antiseptic solutions, antiviral solutions, antibacterial solutions, etc. The term also includes spermicidal solutions, particularly applicable when the protective garment provided by the invention is a condom. The spermicidal solution used is preferably additionally virucidal and/or bactericidal.

The term "impermeable seal" is used to mean a seal which is substantially both fluid-tight and air-tight. The seal should be fluid-tight to prevent leakage of the solution between the layers, and preferably substantially air-tight to facilitate mechanical coupling between the two layers resulting from capillary forces exerted by the solution.

Typical virucides known in the art which may be suitable for use with the present invention include, for example, alcohols, ethers, chloroform, formaldehyde, phenols, beta propiolactone, iodine, chlorine, mercury salts, hydroxylamine, ethylene oxide, ethylene glycol, quaternary ammonium compounds, enzymes, and detergents.

The glove of this invention can provide improved protection over single layer surgical gloves. If the layers of the glove are punctured or torn during surgery, the antimicrobial solution releases and attacks infectious agents before reaching the surgeon's hands, thus protecting the surgeon during operating procedures. Furthermore, when the glove becomes punctured during use, it may act to protect the patient from exposure to germs which may exist on the surgeon's hands. Tearing or puncturing the glove may provide quick and thorough release of the antimicrobial solution disposed between the layers.

Applicant has found that sense of feel is not significantly diminished by double layers with a solution disposed between the layers. By providing a solution layer of thickness in the ranges described above, capillary forces exerted by the liquid solution provide a mechanical-like coupling between the glove layers, so that the sense of feel for the wearer of the gloves is not significantly diminished.

In a preferred embodiment, the antimicrobial solution comprises a virucidal solution, such as aqueous nonoxynol-9. This substance is an effective virucide against such viruses as HIV and hepatitis, and thus provides a glove being particularly useful for performing medical procedures on infected patients. Preferably, the aqueous nonoxynol-9 has a concentration of between about 0.05% and 5% (volume/volume). Most preferably, the concentration is between about 0.25% and 1% (volume/volume). It is known that a concentration in this range is effective for killing viruses. Higher concentrations can also be used but may be irritable if contacted with the eyes.

In another embodiment, the antimicrobial solution comprises a bactericidal solution. Of course, the antimicrobial solution could include both virucidal and bactericidal agents.

In a preferred embodiment of a surgical glove provided by the present invention, the solution includes a dye. This embodiment provides an effective means for showing the surgeon the precise location of a tear or puncture in the glove. Thus, if the outer layer of the glove is punctured, the dye will seep out of the puncture hole and stain the area around the hole. If the inner layer is also punctured, the dye will seep through the inner hole and stain the surgeon's hand at the location of the puncture. This provides the surgeon the precise location of exposure so that the surgeon can decontaminate the area of puncture.

Many suitable dyes are available for use with this invention. A dye should preferably be selected which is FDA approved for internal and external use so as not to harm the patient or surgeon. Preferably, the dye is selected so that its color is easily detectable in a blood environment. Suitable dyes incudes FDA approved FD&C colors, for example, FD&C Blue #1 (MERCK Index #1350), FD&C Blue #2 (MERCK Index #4835), and FD&C Green #3 (MERCK Index #3876). These two dyes are particularly preferred since they have FDA approval for use in food, drugs, and cosmetics, and provide good indications of puncture in use with the present invention due to their intense colors (in relatively low concentrations). Preferably, the concentration of the dye in the solution is between about 0.3 to 0.5 grams/liter, providing a good compromise between economics and tear indication.

Many dyes are also bactericidal and thus provide the further function of attacking infectious agents. Another advantage provided by use of such dyes is that they can not generally be washed off with water. Thus, if the glove is punctured and the user's hand is stained by the dye, he must use alcohol to remove the stain, alcohol also being a bactericide. Thus, the area of the puncture is decontaminated while the dye stain is washed off.

Preferably, the volume of the solution disposed between the layers of an average-sized glove (e.g. size 7.5–8.5) is between about 2 and 3 milliliters. For a size 8.5 glove (surface area approximately 650 $cm^2$), this volume of liquid provides a solution layer thickness of around 0.03 to 0.05 mm, thereby providing good capillary coupling between the glove layers.

In a preferred embodiment, the inner and outer layers are made of latex. Alternatively, the layers may comprise vinyl or neoprene. Latex provides adequate tear resistance for surgical procedures and allows for a good sense of feel for the wearer.

In a preferred embodiment, the inner layer may include a rough outer surface. Alternatively, the outer layer may include a rough inner surface. This may provide the advantage of preventing the solution from being completely squeezed away from any glove areas which are compressed during normal usage.

For applications when one may be exposed to harmful chemicals, such as during handling or preparation of chemicals or other hazardous substances, another embodiment of the present invention provides a protective glove. The protective glove includes an inner layer, an outer layer, an impermeable seal between the inner and outer layers, and a layer of neutralizing solution (thickness as described above) disposed between the inner and outer layers.

The neutralizing solution disposed between the inner and outer layers can be appropriately selected for the particular application for which the glove is to be used. Preferably, the neutralizing solution should be selected such that if the outer layer of the glove is punctured or permeated, the neutralizing solution will neutralize the chemicals to which the glove is exposed and thus protect the hands of the wearer of the glove.

For example, if a chemist is to be handling acids, the neutralizing solution selected should be a basic or buffering solution which could neutralize the acid upon puncture of the glove before reaching the chemist's hands. As another example, if a person were handling neurotoxins one might place appropriate enzymatic agents between the glove layers which could cleave the neurotoxins upon contact.

Since the sense of feel for a chemist is usually not as critical as that for a surgeon, a thicker layer and more protective material than latex is preferably selected for the protective glove. For example, the inner and outer layers may be made of neoprene, nitrile, or any other suitable materials which are resistant to the types of materials to be handled and which are resistant to tearing or puncture.

Since the appropriate neutralizing solution disposed between the layers may vary depending upon the chemicals or materials to be handled, the seal between the layers preferably includes a zip lock seal. In this manner, the user of the glove can temporarily open the seal, place the appropriate neutralizing solution between the glove layers, and reseal the glove.

Additionally, the material between the glove layers may include a pH or other indicator which would change colors after a passage of time to indicate that the neutralizing agent has been used up, such that the gloves may no longer be effective. Upon such indication, the user could replace the old gloves with a new pair.

In a preferred embodiment, the protective solution includes a dye to give a visible warning upon release if the glove is leaking or becomes punctured. That is, the dye upon release will stain the area of puncture.

Another embodiment of the present invention provides a surgical glove including a dye associated with the glove in such a manner as to produce a visible stain if the glove becomes punctured or torn at the location of such puncture or tear.

The invention also extends to a finger cot having an inner layer, an outer layer, an impermeable seal between the layers, and a layer of solution (thickness as described above) disposed between the layers. The finger cot is substantially similar to the surgical glove described above, except that the finger cot is configured and used to cover only a single finger as opposed to an entire hand. The preferred embodiments of materials discussed above in relation to surgical gloves also apply to finger cots. Thus, for example, the antimicrobial solution of a finger cot preferably includes a dye.

The invention further provides a condom having an inner and outer layer, an impermeable seal between the layers, and a layer of solution (thickness as described above) disposed between the inner and outer layers. Preferably, the antimicrobial solution comprises a spermicidal solution, such as nonoxynol-9. Nonoxynol-9 is particularly preferred since it also acts as a virucidal agent for protection against HIV and hepatitis.

In another preferred embodiment the invention provides a glove, condom, or finger cot having an inner layer, an outer layer, an impermeable seal between the layers, and a sealing solution in a middle layer disposed between the inner and outer layers. The sealing solution is operable to fill relatively small holes, ruptures, rips, cracks, and tears in the inner and/or outer layers. Thus the sealing solution may inhibit or prevent bacteria, virus, or microbes from moving through holes in the protective coverings of the present invention. Generally holes of up to about 0.15 mm average diameter may be filled by the sealing solution.

The sealing solution is preferably a hydrogel including corn starch, potato starch, or tapioca. The sealing solution may be used in conjunction with an antimicrobial solution or a dye. The term "sealing solution" means any solution that substantially blocks or fills holes when disposed between the inner or outer layers of a protective covering.

The sealing solution may also be sticky, thus enhancing the adherence of the inner and outer layers together. A further advantage of a sticky sealing solution is that it may be used in protective coverings to adhere the covering to the wearer. For instance, the inner layer in a condom may allow permeation of a small amount of the sealing solution during use such that the condom adheres to the penis.

A further embodiment of the invention provides a protective covering with an inner layer, an outer layer, an impermeable seal between the layers, and a middle layer that inhibits evaporation through the layers. The evaporation inhibitor solution may include a hydrogel. An advantage of the evaporation inhibitor solution is that it inhibits or prevents the solution in the middle layer from evaporating, thus lengthening the time that the coverings may be stored without excessive drying.

One potential problem which can arise with the double (or multi) layer protective coverings provided by this invention is that the two layers may tend to slip on each other during use. This potential problem is most likely to arise when the covering is inserted into and removed from a tight passage, as will typically occur when using a glove, finger cot or condom. To reduce this problem, the layers of the covering may be sealed (e.g., by heat stamping or gluing) at a plurality of points, thereby physically adhering the two layers at those points. This will reduce the likelihood of the layers slipping on each other during use.

It should be appreciated that the protective ability of the covering may be reduced at the sealed points, since a puncture of the covering at that precise location might not cause the release of the protective solution disposed between the layers. This is not likely to present a significant concern in relation to condoms and finger cots, since sharp objects are not generally encountered when using those items. Nevertheless, the potentially reduced protection of the covering should be appreciated and considered when selecting the number and pattern of sealed points on the covering.

Another broad aspect of this invention provides methods for making protective gloves, e.g., surgical gloves. One such method comprises the steps of providing a first glove on a hand-shaped form, the first glove having a hand portion and a wrist portion; dipping the first glove into a solution; placing a second glove having a hand portion and a wrist portion on the hand-shaped form over the first glove, and sealing the wrist portions of said gloves together, such that the solution is contained as a layer between the first and second gloves, the solution layer having an average thickness of less than about 0.12 mm.

A second method provided by this invention comprises the steps of providing a first glove on a hand-shaped form, the first glove having a hand portion and a wrist portion; placing a second glove on the hand-shaped form over the first glove, the second glove having a hand portion and a wrist portion; placing a solution between the first and second gloves, and sealing the wrist portions of said gloves together, such that the solution is contained as a layer (thickness as described above) between the first and second gloves.

The term "hand-shaped form" is used herein broadly to mean any structure having the shape of a human hand, e.g., a conventional ceramic or metal former. The term also encompasses an actual human hand.

The initial step in each of the two above-described methods comprises providing a first glove on a hand-shaped form. This can be accomplished, for example, by obtaining a glove from a commercial or other available source and stretching the glove over a hand-shaped form. Alternatively, it can be accomplished by repeatedly dipping a hand-shaped form into latex or other material to coat the form with a layer of the material, and drying and/or curing the layer to form the first glove on the form.

A third method for making a protective glove provided by this invention comprises the steps of providing a first glove having a hand portion and a wrist portion; exposing the exterior surface of the first glove to a vacuum to expand said gloves placing a solution on the interior surface of the first glove; inserting a second glove having a hand portion and a wrist portion into the expanded first glove; removing the vacuum from the exterior surface of the first glove; and sealing the wrist portions of the first and second gloves together to contain the solution as a layer (thickness as described above) between the first and second gloves.

The first and second gloves in all three methods described above may be, for example, conventional latex surgical gloves, or gloves made of some other material.

Finally, this invention provides a fourth method for making a protective glove comprising the steps of providing an enclosed bag or balloon (i.e., an enveloped sheet of material) having two opposing hand-shaped sections; puncturing one of the hand-shaped sections; applying a vacuum to the interior of the punctured hand-shaped section such that the opposing hand-shaped section is drawn into said punctured section; releasing the vacuum; injecting a solution between the two hand-shaped sections and sealing the puncture, such that the solution is contained as a layer (thickness as described above) between said sections. The enclosed bag of material may be produced in a negative form based on two negative hand-shaped spaces.

A preferred embodiment of each of the above-described methods comprises an additional step of adhering the two hand portions or sections together at a plurality of points. This provides the advantage of restricting slippage of the two hand portions or sections during use of the glove.

The hand portions or sections may be adhered together in a variety of ways, e.g., vulcanization, by gluing, or double-sided adhesive tape.

In a preferred embodiment, the adhering step is accomplished by spot-vulcanizing the hand portions together at a plurality of points. In this embodiment, the first and second gloves (or the enclosed bag in the fourth method described above) may comprise unvulcanized (i.e., green strength) latex. After spot-vulcanizing the hand portions or sections together at the desired points, the entire glove assembly may then be vulcanized. Due to the high temperature involved in such vulcanization, the solution disposed within the glove assembly preferably comprises a degassed liquid, so that the liquid will not emit gas during the vulcanization step.

This invention is now described by reference to the appended drawings which illustrate particular preferred embodiments of this invention.

Figure 1:
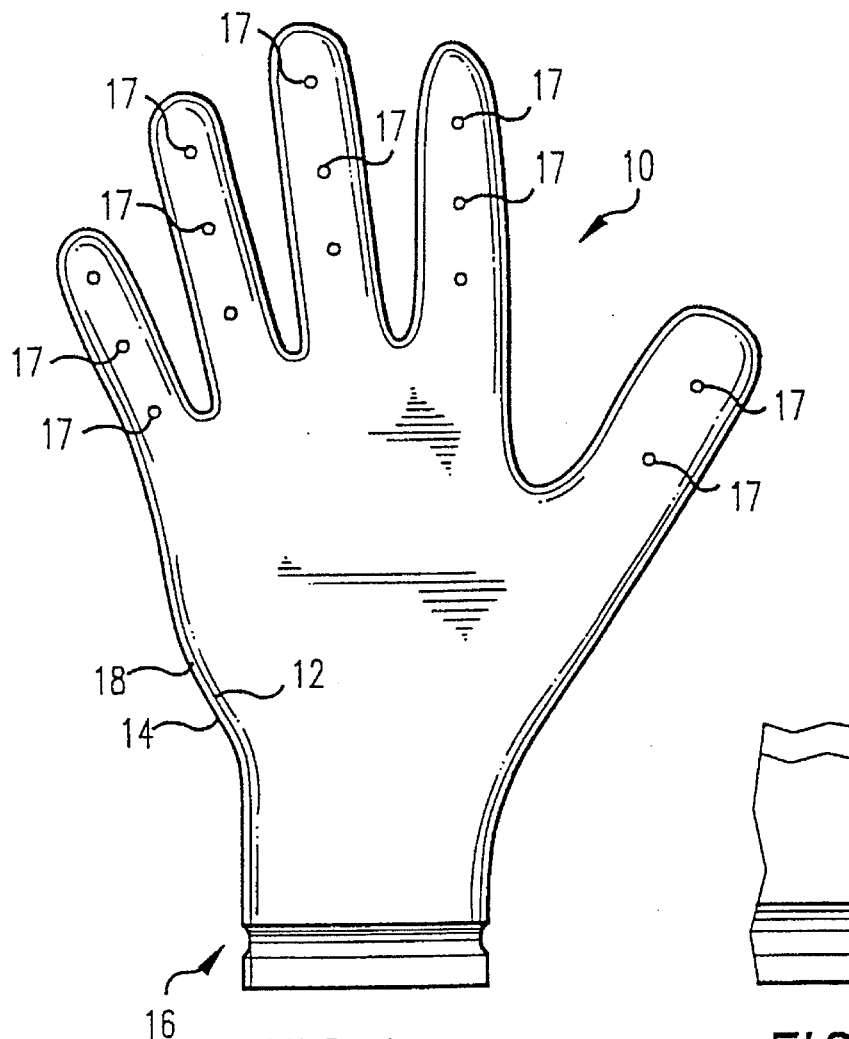
FIG. 1 is a side view of a glove prepared according to the present invention.

Referring now to FIG. 1, a preferred embodiment of the present invention is shown. A double layer glove 10 is illustrated having an inner layer 12, an outer layer 14, an impermeable seal 16 between the inner layer 12 and the outer layer 14, and a solution 18 disposed as a middle layer between the inner layer 12 and the outer layer 14. The solution 18 has an average thickness of less than about 0.12 mm, preferably between about 0.01 and 0.09 mm, even more preferably between about 0.025 and 0.05 mm, thereby maximizing the capillary coupling force between glove layers 12 and 14.

This glove is suitable for a broad range of applications, depending upon the selection of material for the inner and outer layers 12 and 14 and the solution 18. For use as a surgical glove, the inner and outer layers 12 and 14 are preferably made of latex. For such a surgical glove 10, one preferred solution 18 comprises an antimicrobial solution. The antimicrobial solution preferably comprises a virucidal agent such as nonoxynol-9. The antimicrobial solution may also or alternatively include a bactericidal solution.

In a preferred embodiment, the solution 18 includes a dye. The dye will stain the area surrounding a puncture or tear in the glove, giving the surgeon a visual means for detecting areas of exposure.

In a preferred embodiment of the invention, the antimicrobial solution comprises nonoxynol-9 having a concentration of between about 0.05%–5% (v/v), most preferably about 0.5% (v/v), and a dye comprising FD&C Blue #1 having a concentration of between about 0.3 and 0.5 g/l.

In one preferred embodiment, the inner layer 12 includes a rough outer surface (i.e., the surface exposed to the antimicrobial solution 18). Single layer latex gloves are commercially available, wherein one may specify the roughness or coarseness of the surfaces of the glove.

In another preferred embodiment, the solution 18 preferably comprises a sealing solution that is operable to seal relatively small holes in the inner layer 12 or the outer layer 14. Thus if either the inner layer 12 or outer layer 14 includes or develops relatively small holes, then the sealing solution 18 fills and seals the resulting holes. In this manner the gloves provide additional protection for the wearer and the patient, since holes in the glove that might allow transmission of microbes, viruses, bacteria, etc. become substantially filled and sealed with the sealing solution. "Holes," as used herein, means relatively small holes, gaps, cracks and other imperfections that would allow a fluid to permeate the inner layer 12 or the outer layer 14.

Preferably the sealing solution 18 comprises a hydrogel. Hydrogels generally act to physically block or plug holes that form in the inner layer 12 or the outer layer 14. The term "hydrogel" means a three-dimensional cross-linked network which swells, but does not dissolve, in an aqueous environment. The cross-linking is usually covalent or ionic, but hydrogels may also be generated by linear amphipathic block copolymers, or block graft copolymers. In general, as the water content of a hydrogel increases, the physical properties, such as modulus and strength, tend to decrease.

Synthetic hydrogels are usually prepared by the copolymerization of hydrophilic monomers, notably hydroxyethyl methacrylate, in the presence of a cross-linking agent. An alternative synthetic approach is the conversion of existing polymers to a hydrophilic but water insoluble product.

Hydrogels generally work well in the sealing solution because: 1) anti-vital, anti-bacterial or other desirable compounds may be mixed with a hydrogel, 2) hydrogels trapped between two layers tend to relatively quickly fill holes, and 3) hydrogels have been found to inhibit evaporation of other solutions in the middle layer (such as antimicrobial solutions).

Hydrogels include natural hydrogels, or synthetic natural-based hydrogels, or synthetic hydrogels. Natural hydrogels are often sticky and deformable exudates from plants such as gum arabic, gum karaya, and gum ghatti. These exudates include polysaccharides containing various sugars other than glucose, and with significant quantities of oxidized groups as an adjunct to their normal polyhydroxy format. Some of these groups are carboxyl-groups found as salts of calcium, magnesium or potassium.

Another group of natural hydrogels include such compounds as agar, alginate and pectin. These compounds are generally derived from land and marine plants and their seeds by extraction or fractionation. These compounds are generally salts of acidic polysaccharides, and generally have a more variable and complex polymer structure than the exudates.

Other natural hydrogels that may be used include carrageenan (kappa, lambda, iota) food grade (about 0.1– 6.9, preferably 0.1–2.0, and more preferably 0.2–0.8 weight percent), guar gum food grade (about 0.35–6.0, preferably 0.35–2.0, and more preferably 0.4–0.6 weight percent), agar (about 0.2–2.4, preferably 0.3–1.8, and more preferably 0.5–1.0 weight percent), gum arabic (about 1.0–70.0, preferably 15.0–50.0, and more preferably 25.0–35.0 weight percent), locust bean gum (about 0.1–1.0, preferably 0.30–0.80, and more preferably 0.40–0.60 weight percent), pectins such as high methoxyl pectin, National Formulary XII Type (about 0.1–3.0, preferably 0.30–2.0, and more preferably 0.50–1.00 weight percent) and low methoxy pectin (about 0.4–2.0, preferably 0.5–1.50, and more preferably 0.8–1.20 weight percent), and xanthum gum (about 0.15–9.6, preferably 0.20–2.50, and more preferably 0.40–1.35 weight percent).

Starches may also be used as hydrogel compounds. Preferred starches are those starches classified as GRAS (Generally Recognized As Safe) or Food Starch-Modified with a high amylose content such as corn starch (about 22–28% amylose), tapioca starch (about 17–22% amylose), potato starch (about 20–25% amylose), sorghum starch (about 23–28% amylose), wheat starch (about 17–27% amylose), sago starch (about 23–29% amylose), and amylomaize starch (about 50–80% amylose). These starches generally form relatively strong unsupported films and gels. A preferred starch is corn starch due its relatively low cost, its ready availability, and the relatively high viscosity of its hydrogels. The viscosity of starch hydrogels such as corn starch may be further enhanced by sucrose (preferably up to about 20 weight percent sucrose).

Pregelatinized or crosslinked starches or dextrins may also be used as hydrogels in the subject invention. Corn dextrin generally has relatively good adhesion properties. The addition of humectants such as sorbitol, glycerol, sugar, corn syrup and other polyhydroxy compounds may help to retain moisture in the hydrogels. Borax (sodium tetraborate) tends to increases the viscosity and stability of the hydrogel and tends to make it more cohesive and tacky. The addition of sodium hydroxide (preferably about 0.5–1.5 weight percent) to the dextrin gel tends to also enhance viscosity, stability and tack.

In a preferred embodiment corn starch in the form of Food Starch-Modified may be used (about 2–12, preferably about 4–10, more preferably about 5–8 weight percent, and more preferably still about 6.0 weight percent in water). Sucrose may also be preferably added to the corn starch (preferably about 2–20, more preferably about 6–16, and more preferably still about 9–13 weight percent of the mixture includes sucrose). Nonoxynol-9 may also be added to the corn starch or the corn starch/sucrose mixture (preferably about 0.5–5 weight percent).

Synthetic natural-based hydrogels may include compounds that are produced by derivatization of the hydroxyl groups of cellulose and starch. For instance carboxymethylcellulose may be used as such. Another group of synthetic natural-based hydrogels includes those compounds based on neutral ethers such as methyl, ethyl, hydroxymethyl and hydroxypropyl derivatives of cellulose and starch. Still another group is based on grafting vinyl-type monomers on free cellulose and starch radicals, and on subsequent crosslinking.

A preferred synthetic natural-based hydrogel may include methylcellulose (present in weight percent of about 2.4–11.0, preferably 3.2–8.5, and more preferably 4.0–6.5), hydroxypropylmethylcellulose (present in weight percent of about 0.10–1.20, preferably 0.2–0.8, and more preferably 0.40–0.65), carboxymethylcellulose food grade (present in weight percent of about 2.0–10.0, preferably 3.25–7.0, and more preferably 5.0–6.0), or hydroxypropylcellulose (present in weight percent of about 1.0–5.0, preferably 2.0–4.0, and more preferably 2.5–3.5).

Synthetic hydrogels include such compounds as polyvinylalcohol, polyacrylamide, and polyethylene glycol. These hydrogels may be prepared by polymerization of simple molecules such as vinyl-, acrylic-, and polyether-type monomers.

Other synthetic hydrogels include polyethylene glycol with a molecular weight of about 400 (present in weight percent of about 37.0–60.0, preferably 40.0–50.0, and more preferably 42.0–48.0), and polyethylene glycol with a molecular weight of about 4000 (present in weight percent of about 30.0–60.0, preferably 40.0–50.0, and more preferably 43.0–46.0). Polyethylene oxide (molecular weight of about 60,000) may be used (preferably weight percent of about 0.1–1.5, more preferably 0.3–1.0, and more preferably still 0.4–0.6). Polyvinylpyrrolidone (molecular weight of about 20000) may be used in weight percent of about 1.0–7.5, preferably 2.0–5.0, and more preferably 2.5–3.5. Hydroxyethyl methacrylate, polyhydroxyalkyl methacrylates, and polymethacrylamide and derivatives may also be used as hydrogels.

The sealing solution may comprise an emulsifier or a surfactant. In general, hydration of starch granules, swelling and solubilization are enhanced by using surfactants. Sodium lauryl sulfate (preferably about 1.0–10.0, more preferably about 3.0–7.0, and more preferably still about 4.0–6.0 weight percent) may act as a wetting agent for corn and potato starches above 85° C.

The sealing solution preferably comprises an antimicrobial solution to kill viruses, bacteria, and microbes that permeate holes in the inner or outer layers. The antimicrobial solution is particularly useful for use with a sealing solution since the sealing solution itself may be a favorable environment for viruses, bacteria, or microbes. A preferred antimicrobial solution used with the hydrogel sealing solution is nonoxynol-9, which is an effective antimicrobial solution and which tends to act as an emulsifier for hydrogels (such as corn starch) in water. Nonoxynol-9 is a particularly preferred antimicrobial compound because nonoxynol-9 also tends to act as a surfactant, and also tends to enhance hydration, swelling, and solubilization of some starch granules used to prepare the hydrogel. In general, the amount of preferred antimicrobial solution is the same as described above for other multilayer coverings. Dyes in the amount and type described above may also be used with the sealing solution.

The sealing solution preferably fills holes of up to about 0.07 mm average diameter, more preferably up to about 0.10 mm average diameter, even more preferably up to about 0.15 mm average diameter. As the sizes of the holes increase, the difficulty of filling such holes with the sealing solutions correspondingly increases. Certain inner layer 12 and outer layer 14 embodiments are more susceptible to holes, depending on the materials and thicknesses of the layers. Thus, different sealing solutions, and different viscosity of sealing solutions may be preferred for different embodiments. For instance, it is anticipated that for surgical gloves the latex used for the inner and outer layers will be relatively thin, and thus a higher concentration of sealing solution within the inner layer is preferred. In addition, antimicrobial solutions such as nonoxynol-9 tend to help mix some hydrogels such as corn starch in water.

The volume of sealing solution is preferably 2–3 ml for a size 7.5–8.5 glove, preferably 0.2–0.3 ml for a condom, and preferably 0.1–0.2 ml for a finger cot.

Preferably the sealing solution is substantially uniformly distributed between the inner layer 12 and outer layer 14. Preferably the layer of sealing solution has an average thickness of less than about 0.12 mm. More preferably the layer of sealing solution has an average thickness of between about 0.01 and 0.09 mm. Even more preferably, the layer of sealing solution has an average thickness of between about 0.025 mm and 0.05 mm, thereby maximizing the capillary coupling force between glove layers 12 and 14.

In another preferred embodiment of the invention the sealing solution 18 adheres the inner layer 12 to the outer layer 14. The adhesive or "sticky" characteristic of the sealing solution may facilitate sense of feel for the wearer of the covering because it: 1) may inhibit misalignment of the inner layer 12 from the outer layer 14, and 2) may increase sensitivity by eliminating slippage of the inner and outer layers.

The adhesive feature of the sealing solution in this embodiment may also tend to enhance adhesion of the wearer to the protective covering. The adhesion may be enhanced when relatively small amounts of sealing solution leak through the covering and provide sticky solution which moderately adheres the wearer to the covering. This feature may be of particular importance when the invention is embodied in a condom. During intercourse, the condom typically becomes subjected to stress, which, depending on the material and thickness of the inner layer 12, tends to force relatively small amounts of sealing solution through holes in the inner layer 12. The sealing solution then provides a moderate amount of adherence of the male organ to the condom. In this manner post-coital slippage of the condom is prevented, which results after the male organ becomes too flaccid to hold the condom by tension. Such post-coital slippage may result in unwanted contact between male and female body fluids or body parts, which may result in infection or pregnancy.

Preferably the solution 18 resists evaporation. In this manner protective coverings such as gloves, condoms, and finger cots may remain hydrated longer, resist cracking longer, and have a longer shelf life. Preferably the solution 18 includes a hydrogel to resist evaporation.

EVAPORATION RESISTANCE EXAMPLES

Figure 9:
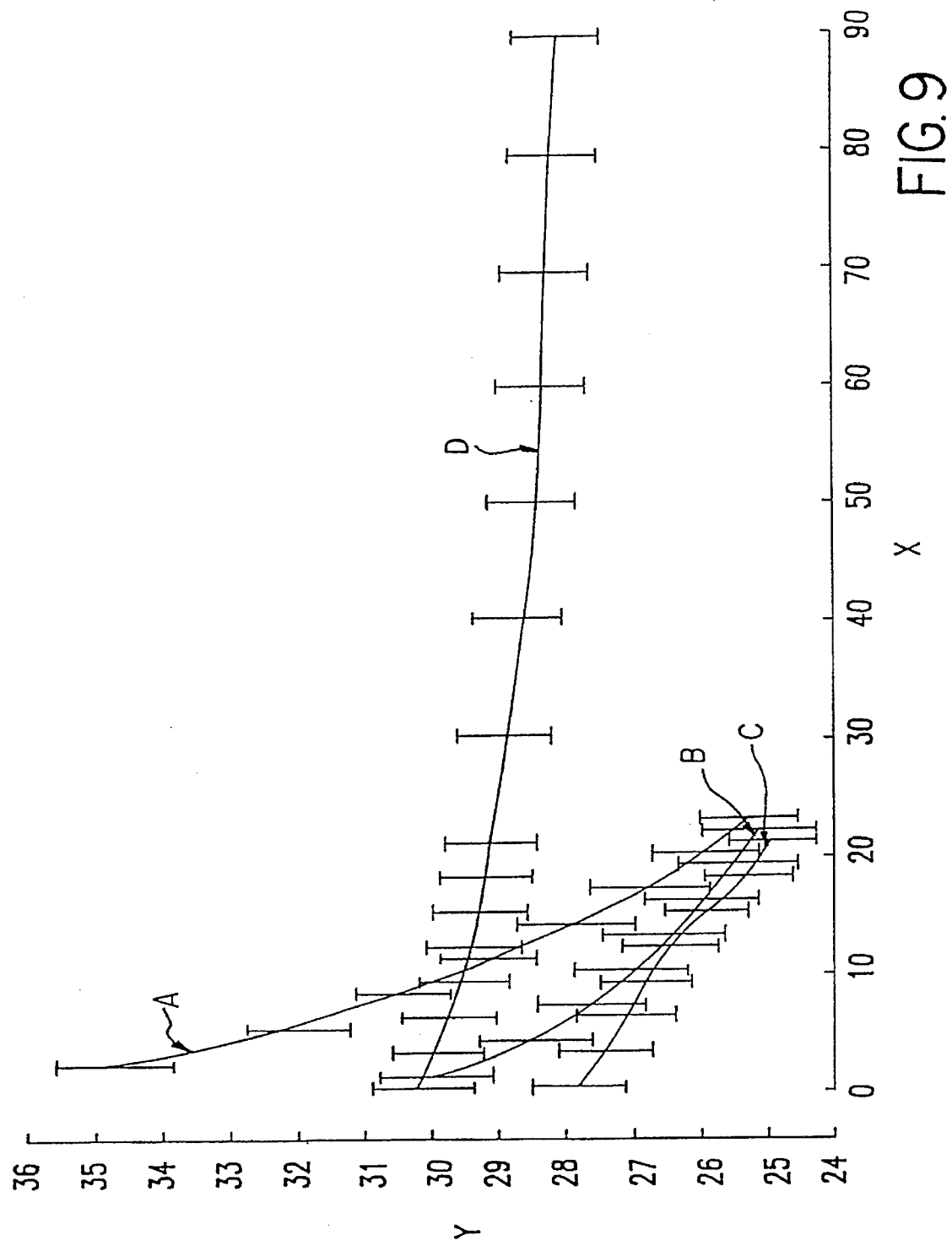
FIG. 9 is a plot of experimental results showing the mass of various gloves (see Y-axis, numbered in grams) as a function of time (see X-axis, numbered in day units).

FIG. 9 shows the relative evaporation resistance of gloves with a solution 18 that included a hydrogel. In FIG. 9, time is plotted on the "X" axis and mass (grams) of gloves is plotted on the "Y" axis. Each point on FIG. 9 is represented by an elongated "I." Each "I" represents the variation in mass of ten gloves measured on a given day, with the average mass of the ten gloves being the midpoint of each "I." The gloves tested were Becton Dickinson "Desert Tradition Surgical Gloves," size 7.5, Catalog #376199, Becton Dickinson Acute Care Division (Franklin lakes, N.J., U.S.A.).

Four types of gloves were tested for mass change as a function of time. Sample group or curve "A" represents gloves of the invention wherein solution 18 included 10 milliliters ("ml") of 0.4 weight percent dye and 1.0 weight percent nonoxynol-9 in water. Sample group or curve "B" is the same solution as in sample group or curve "A" except the total solution volume was only 5 ml. Sample group or curve "C" is the same solution as in sample group or curve "A" except the total solution volume was only 3 ml. Sample group or curve "D" represents gloves wherein solution 18 included 5.0 ml of 6.0 weight percent corn starch, 0.4 weight percent dye, and 1.0 weight percent nonoxynol-9. The solutions were sealed in the middle layer with rubber glue. Gentle rolling action was applied to distribute the solutions evenly in the middle layer.

All gloves were left unprotected at room conditions of approximately 18°–21° C. and approximately 50% relative humidity. The gloves were stored in cardboard boxes in a substantially dark cupboard.

Figure 10:
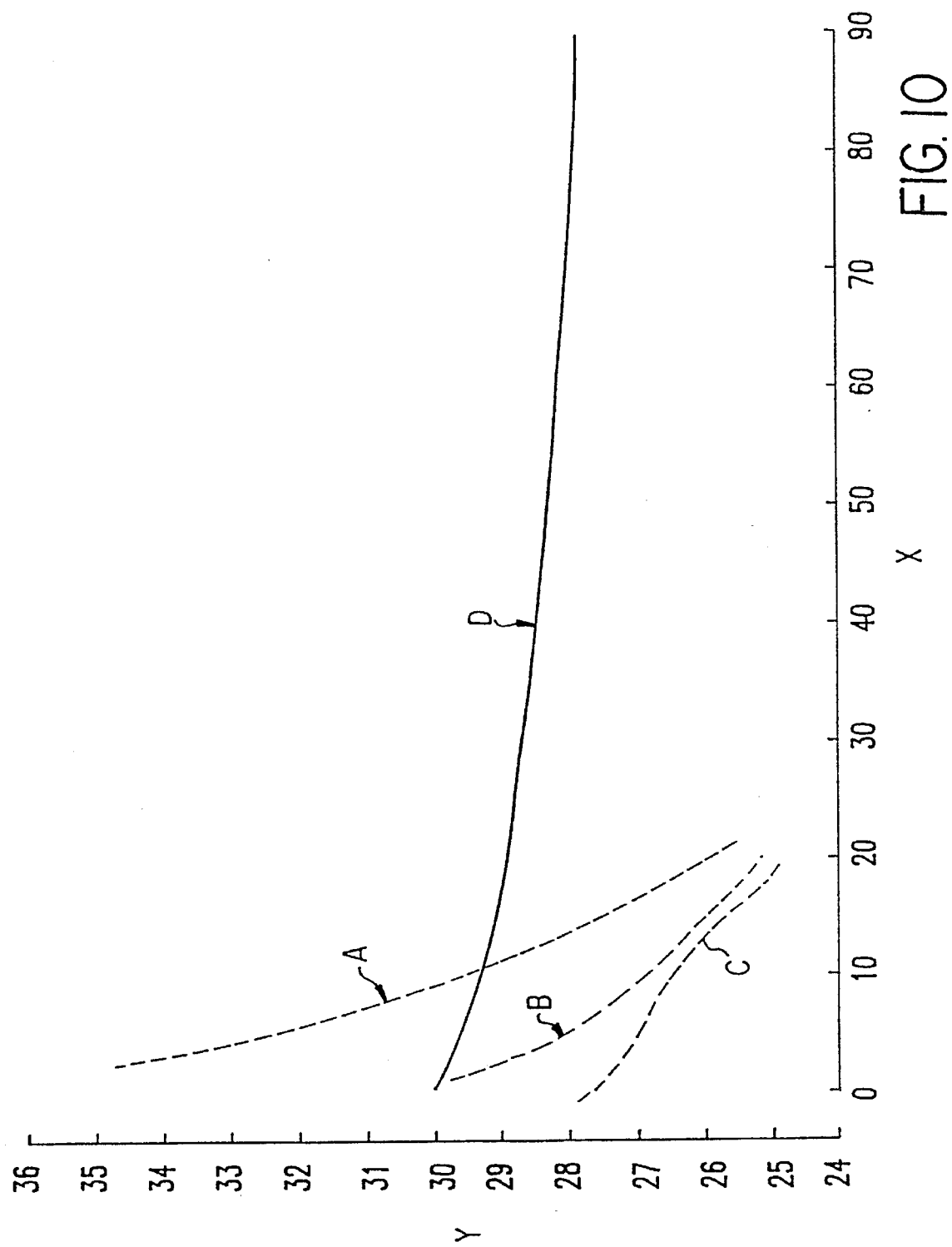
FIG. 10 is a plot of experimental results showing the mass of various gloves (see Y-axis, numbered in grams) as a function of time (see X-axis, numbered in day units).

As shown in FIG. 9 the gloves with a hydrogel in the solution 18 (i.e. curve "D") had a greater mass stability as a function of time. It is believed that the greater mass stability of the gloves with hydrogels resulted because the hydrogels tended to inhibit evaporation of the solution 18. It is also believed that the hydrogels prevented drying of the inner layer 12 and the outer layer 14 since these layers were constantly kept in contact with a larger amount of aqueous solution 18 due to the presence of the hydrogels. Since drying of gloves is a major cause of glove deterioration over time, it is believed that the gloves of the present invention will have an enhanced shelf life. FIG. 10 shows sample group curves without the "I" shaped lines.

As shown in FIGS. 9 and 10, gloves in sample groups "A," "B" and "C" all reduced to below about 26.0 grams in less than about 24 days. Gloves using hydrogel (sample group "D") maintained most of their mass even after 90 days.

Figure 11:
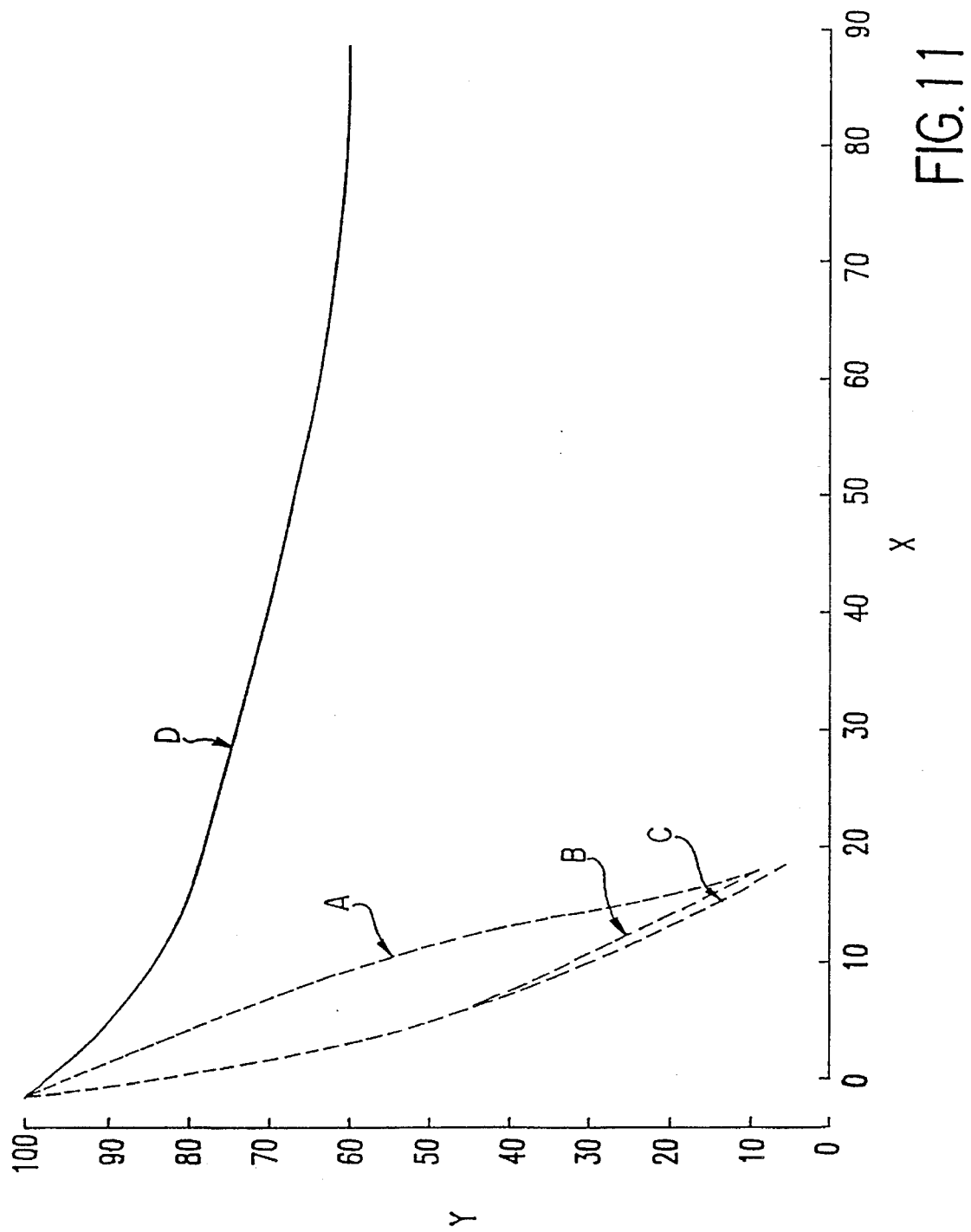
FIG. 11 is a plot of the percent solution remaining in various gloves (see Y-axis, numbered in percent) as a function of time (see X-axis, numbered in day units).

Table A shows the quantitative results for the double layer ("D-L") glove time curve shown in FIGS. 9 and 10. Table A shows the mean weight (with standard deviation calculations) of ten gloves at various time intervals. The mean weight was used to determine the amount of solution remaining, based on the assumption that the glove latex layers themselves lost negligible weight over time. Table A shows the percent of solution that remained, as a function of the initial solution present. FIG. 11 shows the a graph of the percent of solution that remained for the four sample groups.

TABLE A

| | DAY 0 | DAY 3 | DAY 6 | DAY 9 | DAY 12 | DAY 15 | DAY 18 | DAY 21 |
|---|---|---|---|---|---|---|---|---|
| DOUBLE LAYER GLOVE 10 ML AQUEOUS SOLUTION - CURVE A (N = 10 D-L GLOVES) | | | | | | | | |
| MEAN | 34.72 | 31.89 | 30.31 | 29.06 | 27.82 | 26.77 | 25.97 | 25.35 |
| STD. DEV. | 0.61 | 0.74 | 0.73 | 0.71 | 0.85 | 0.88 | 0.79 | 0.72 |
| % REMAINING | | | | | | | | |
| % REMAINING | 100.00 | 71.47 | 55.54 | 42.94 | 30.44 | 19.86 | 11.79 | 5.54 |
| DOUBLE LAYER GLOVE 5 ML AQUEOUS SOLUTION - CURVE B (N = 10 D-L GLOVES) | | | | | | | | |
| MEAN | 24.92 | 28.40 | 27.61 | 27.04 | 26.57 | 26.05 | 25.51 | 25.22 |
| STD. DEV. | 0.81 | 0.83 | 0.77 | 0.81 | 0.90 | 0.82 | 0.88 | 0.83 |
| % REMAINING | | | | | | | | |
| % REMAINING | 100.0 | 70.31 | 54.88 | 43.75 | 34.57 | 24.41 | 13.87 | 8.20 |

TABLE A-continued

| | DOUBLE LAYER GLOVE 3 ML AQUEOUS SOLUTION - CURVE C (N = 10 D-L GLOVES) | | | | | | | |
|---|---|---|---|---|---|---|---|---|
| MEAN | 27.79 | 27.42 | 27.11 | 26.85 | 26.51 | 25.98 | 25.37 | 25.01 |
| STD. DEV. | 0.68 | 0.67 | 0.70 | 0.65 | 0.69 | 0.64 | 0.66 | 0.65 |
| % REMAINING | | | | | | | | |
| % REMAINING | 100.0 | 87.63 | 77.26 | 68.56 | 57.19 | 39.46 | 19.06 | 7.02 |
| | DOUBLE LAYER GLOVE 5 ML HYDROGEL - CURVE D (N = 10 D-L GLOVES) | | | | | | | |
| MEAN | 30.15 | 29.81 | 29.64 | 29.43 | 29.29 | 29.19 | 29.10 | 29.01 |
| STD. DEV. | 0.70 | 0.66 | 0.69 | 0.68 | 0.70 | 0.70 | 0.68 | 0.67 |
| % REMAINING | | | | | | | | |
| % REMAINING | 100.00 | 93.64 | 90.47 | 86.54 | 83.93 | 82.06 | 80.37 | 78.69 |

| | DAY 30 | DAY 40 | DAY 50 | DAY 60 | DAY 70 | DAY 80 | DAY 90 |
|---|---|---|---|---|---|---|---|
| | DOUBLE LAYER GLOVE 5 ML HYDROGEL - CURVE D (N = 10 D-L GLOVES) | | | | | | |
| MEAN | 28.83 | 28.64 | 28.45 | 28.33 | 28.25 | 28.14 | 28.11 |
| STD. DEV. | 0.69 | 0.66 | 0.65 | 0.64 | 0.63 | 0.65 | 0.64 |
| % REMAINING | | | | | | | |
| % REMAINING | 75.33 | 71.78 | 68.22 | 65.98 | 64.49 | 62.43 | 61.87 |

Nonsterile protective coverings such as gloves, condoms, or finger cots that include a solution to inhibit evaporation may be packaged and stored in plain cardboard boxes, thus reducing packaging costs. Sterile coverings may be stored in like manner, except that the sterile coverings may be individually packaged in plastic. Coverings that include a solution 18 that is not evaporation-inhibited will tend to dry out relatively quickly at ambient conditions, as shown in FIG. 9.

Preferably gloves, condoms, and finger cots of the present invention have at least as good a sense of feel as a single 0.2 mm thick latex layer. That is, the sense of feel for coverings of the present invention is generally at least as good as the sense of feel for single layer latex coverings of substantially the same overall thickness. It is anticipated that some gloves, condoms, and finger cots of the present invention will have a sense of feel at least as good as the sense of feel of a single 0.2 mm thick latex layer, but no better than the sense of feel of a single 0.1 mm thick latex layer.

An alternate embodiment of the invention includes coverings such as condoms adaptable to adhere to the wearer of such coverings. These coverings may be made as described above, except that the inner layer may be formed with imperfections and holes. The inner layer may thus be adapted to leak solution from the middle layer, through the inner layer, and to the wearer during use. The solution in the middle layer preferably includes a skin-adherent, and the covering thus adheres to the wearer during use.

An inner layer with imperfections and holes may be made by dipping a form into layer-forming solution such as latex that includes a relatively large amount of PDMS (about 0.1–2.5% weight percent, preferably about 0.5–2.0, and more preferably about 0.5–1.0). The PDMS tends to produce holes that are about 1.0–2.0 mm diameter and cracks about 1.0–4.0 mm in length. The concentration of PDMS in the inner layer-forming solution may be optimized to: a) produce a desired amount of holes, b) facilitate subsequent donning of the condom, and c) make the middle layer stick to the first layer.

With the exception of the inner layer, the covering may be made as described above, except that the middle layer may also include a skin-adherent with gum karaya (about 80–98 weight percent, more preferably about 85–95 weight percent, and more preferably still about 88–92 weight percent), polyethylene oxide (molecular weight 40,000) (about 2–7 weight percent, more preferably about 3–6 weight percent, and more preferably still about 3.5–5.0 weight percent), and mineral oil (about 5–20 weight percent, more preferably about 7–15 weight percent, and more preferably still about 8–12 weight percent). In addition, other hydrogels such a mentioned above may also be used as skin-adherents.

A middle layer that includes a skin adherent may tend to exhibit high tackiness when wetted. The skin-adherent may also be deposited on the inside of a conventional single layer condom. The basic principle of this embodiment of the invention is to have relatively high wet tackiness on the inside of the covering and relatively low tackiness on the outside of the condom.

In a preferred embodiment, the layers 12 and 14 are sealed (i.e., adhered) together at a plurality of points to reduce the likelihood that the layers will slip on each other during use. As shown in FIG. 1, the fingers the glove 10 may include a plurality of points 17 where the layers 12 and 14 have been adhered together. This feature is particularly advantageous when the fingers are used to explore or examine tight places. As illustrated in FIG. 1, the adhered points 17 are preferably located at the dorsal midpoint of the distal, middle, and proximal phalanges of each finger. By locating the points at the dorsal portion of the glove 10, sensitivity is not substantially impaired, but slippage of the layers is restricted.

The adhered points may be formed by heating and pressing the inner and outer layers together at the desired places for a sufficient length of time for a seal to form. Alternatively, the layers may simply be glued together, or stuck together with double-sided adhesive tape, available commercially from, e.g., the 3M Company.

Figure 1A:
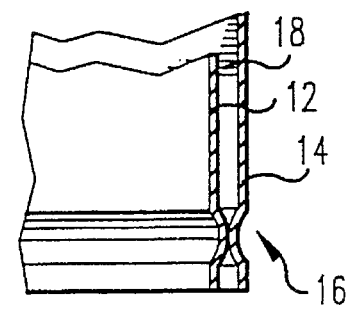
FIG. 1A is an enlarged, fragmentary, sectional side view illustrating the impermeable seal between the inner and outer layers of the glove of FIG. 1.
Figure 2:
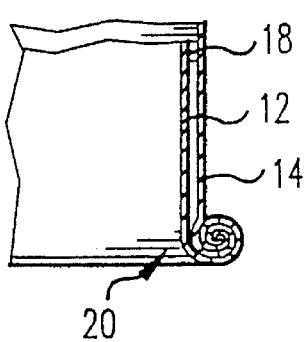
FIG. 2 is a fragmentary, sectional side view illustrating an alternate impermeable seal between the inner and outer layers of a glove in accordance with the present invention.
Figure 3:
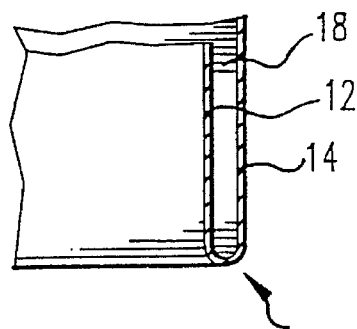
FIG. 3 is also a fragmentary, sectional side view showing another alternative of an impermeable seal.

The impermeable seal between the inner and outer layers 12 and 14 may take a variety of forms as illustrated in FIGS. 1A, 2 and 3. In FIG. 1A, the inner and outer layers 12 and 14 proximate the wrist area of the glove have been vulcanized or heat stamped to provide an impermeable seal 16. The seal 16 can be formed by simply applying heat and pressing the inner and outer layers 12 and 14 together around the circumference of the wrist area for a sufficient length of time for a seal to form.

Alternatively, inner layer 12 and outer layer 14 may be glued together to form an impermeable seal 20 as shown in FIG. 2. For example, with respect to a latex surgical glove, a latex glue can be conveniently used. Such glues are commercially available, e.g., 2141 Rubber Adhesive from the 3M Company. Alternatively, commercially available rubber cements can be used to create the seal between the layers. As a further alternative, shown in FIG. 3, inner layer 12 and outer layer 14 may be formed of a continuous sheet of material such that an impermeable seal 22 is provided by the roll connecting the inner and outer layers 12 and 14. Other fluid-tight seals may be used, for example, tape adhesive on both sides or a zip lock seal.

For chemical handling or preparation applications, the inner and outer layers 12 and 14 shown in FIG. 1 preferably comprise either neoprene or nitrile. A neutralizing solution 18 is disposed between the inner and outer layers 12 and 14. Furthermore, the seal 16 is preferably a zip lock type seal, so that the user can select and place an appropriate neutralizing solution between the layers depending upon the particular chemicals to be handled.

Several methods of preparing gloves provided by the present invention will now be described. These preparations will be discussed in the context of surgical gloves, although it should be understood that analogous preparations may be performed for other types of gloves and protective coverings.

In one preferred method, one places a first glove on his hand (or hand-shaped form). This first glove will eventually form the inner layer of a double-layer glove. The preparer of the glove dips his gloved hand into a solution and removes his hand from the solution. The preparer then places a second glove on his hand over the first glove. The second glove thus forms the outer layer of the double-layer glove. To form an impermeable seal between the first and second gloves, the preparer may peel a portion of the second glove away from his wrist. The preparer then applies glue or double adhesive tape to the outer surface of the first glove around the periphery proximate the wrist of the glove. The preparer then peels the wrist area of the second glove back over the first glove to form a glue seal.

In another preferred method, one places a first glove on a hand-shaped form. Next, glue or double-sided adhesive tape is placed at various points on the exterior of the first glove. Next, a second glove is placed over the first glove, whereby the glue or double-sided adhesive tape adheres the two gloves together at a plurality of points. Next, a solution is placed between the first and second gloves, e.g., by injecting the solution therebetween. Finally, the wrist portions of the two gloves are sealed (e.g., with glue or double-sided adhesive tape) to contain the solution between the two gloves.

In another preferred method, one dips a hand-shaped form (e.g., a ceramic former) in latex to form a layer of latex on the form. When the layer is sufficiently dry, a first "green" glove is thereby provided on the hand-shaped form. A second green strength (i.e., unvulcanized) latex glove is placed over the first glove, and a degassed liquid is disposed between the two gloves. (This may be accomplished either by dipping the first glove in the degassed solution liquid prior to applying the second glove, or injecting the degassed liquid between the two gloves after applying the second glove). Next, the wrist portions of the two gloves are adhered together by vulcanization to form an impermeable seal, thereby containing the solution between the two gloves. The two gloves may be adhered together at a plurality of points by spot-vulcanizing them together at desired spots. Finally, the entire glove assembly is vulcanized.

Another suitable method of preparing a double-layer glove includes providing a first glove and exposing the exterior of the first glove to a vacuum environment. This first glove will eventually form the outer layer of the double-layer glove provided by the present invention. For example, the first glove may be inserted into a box through a box opening, wherein the wrist area of the first glove is temporarily sealed over the opening of the box in an air-tight arrangement. A vacuum is then applied to the interior of the box. This operates to expand the first glove like a balloon.

Next, a selected amount of solution is placed into the interior of the first glove. A second glove, which will form the inner layer of the double-layer glove, is now inserted into the expanded first glove. Preferably, the second glove is provided on a production form in the shape of a hand so that the second glove may be conveniently inserted in proper finger alignment with the first glove. The vacuum is then released and the first glove is released from the box opening. The first and second layers are then sealed proximate the wrist area.

A double-layer glove may be formed from a single piece of material, and thus provide a glove having a rolled seal as illustrated in FIG. 3. To make such a glove, a sheet of latex is first formed having two opposing glove-shaped sections. Such a sheet may be made using a negative form. Thus, one half of the sheet is in the shape of a hand, and the other half of the sheet is in the shape of an opposing hand. A puncture is made in one of the opposing hand sections and a vacuum is applied to the interior portion of that hand section. Due to the vacuum, the opposing hand section will be drawn into the first hand to provide a double layer glove. The hand section in which the puncture was made and vacuum applied forms the outer layer, and the opposing hand section forms the inner layer. The vacuum is then released and a selected amount of solution is injected between the two hand sections through the puncture opening in the outer glove section. The puncture opening is then sealed.

Figure 4:
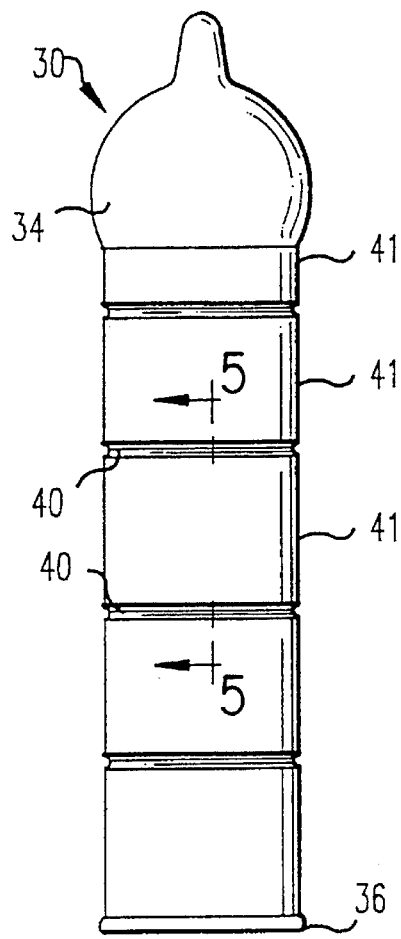
FIG. 4 is a side view of a condom prepared according to the present invention.
Figure 5:
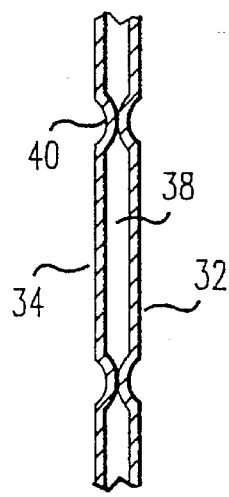
FIG. 5 is a fragmentary, sectional view of the condom taken at the position shown in FIG. 4.

Referring now to FIGS. 4 and 5, a preferred embodiment of a condom 30 as provided by the present invention is illustrated. The condom 30 includes an inner layer 32, and outer layer 34, and an impermeable seal 36 between the inner and outer layers at the rim of the condom. A layer of solution 38 (thickness as described above), such as spermicidal nonoxynol-9, is disposed between the inner layer 32 and outer layer 34. Nonoxynol-9 is preferred, as it is both spermicidal to reduce the risk of pregnancy and virucidal for protection against harmful viruses such as HIV. Alternatively, a sealing or evaporation inhibitor solution may be used. The layers may be made of materials conventionally used for making condoms.

In order to reduce the likelihood of the layers 32 and 34 from slipping on each other during use, the layers may be sealed together at a plurality of points. In the embodiment shown, the condom 30 is provided with a plurality of circular heat stamped lines 40, dividing the condom into distinct compartments 41 along its length. In this arrangement, the protective fluid 38 may be prevented from squeezing to the base of the condom during use, as each heat stamped line 40 will restrict fluid flow between adjacent compartments 41. The heat stamped lines may be formed by heating and pressing the inner and outer layers together at the desired places for a sufficient length of time for a seal to form.

Figure 6:
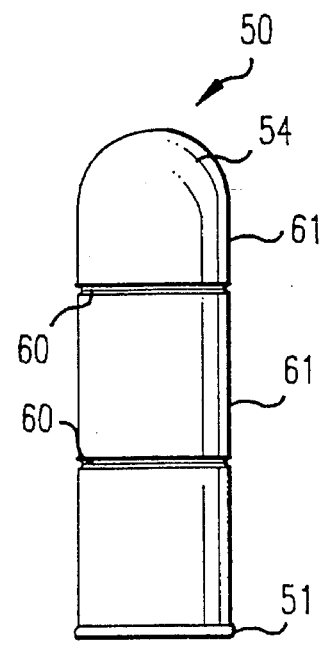
FIG. 6 is a side view of a finger cot prepared according to the present invention.

Referring now to FIG. 6, a preferred embodiment of a finger cot 50 is illustrated. Similar to the surgical glove described above, the finger cot 50 includes an inner layer, an outer layer 54, an impermeable seal 56 between the inner and outer layers, and a layer of solution (thickness as described above) disposed between the layers. (It should be noted that a sectional view of the sidewall of the finger cot would look substantially similar to FIG. 5). The preferred materials for use as the layers and solution discussed above in connection with surgical gloves also apply to the finger cot 50.

Since finger cots are conventionally used for procedures such as rectal or vaginal examinations, it is desirable to seal the inner layer 52 and outer layer 54 together at a plurality of points to reduce the likelihood of disassembly during use. In the embodiment shown, the finger cot 50 is heat stamped with several circular lines 60, compartmentalizing the finger cot into isolated sections 61. As with the condom described above, this embodiment prevents the solution from accumulating at the base of the finger cot during use.

EXAMPLE

The following experiment was designed to demonstrate the capillary coupling force exerted by a liquid layer between two latex surfaces as a function of the thickness of the liquid layer. This was accomplished by measuring the average failure load ("AFL") in g/cm$^2$, between two glass carriers coated with vulcanized latex, having a fluid layer of varying thickness therebetween.

Figure 7:
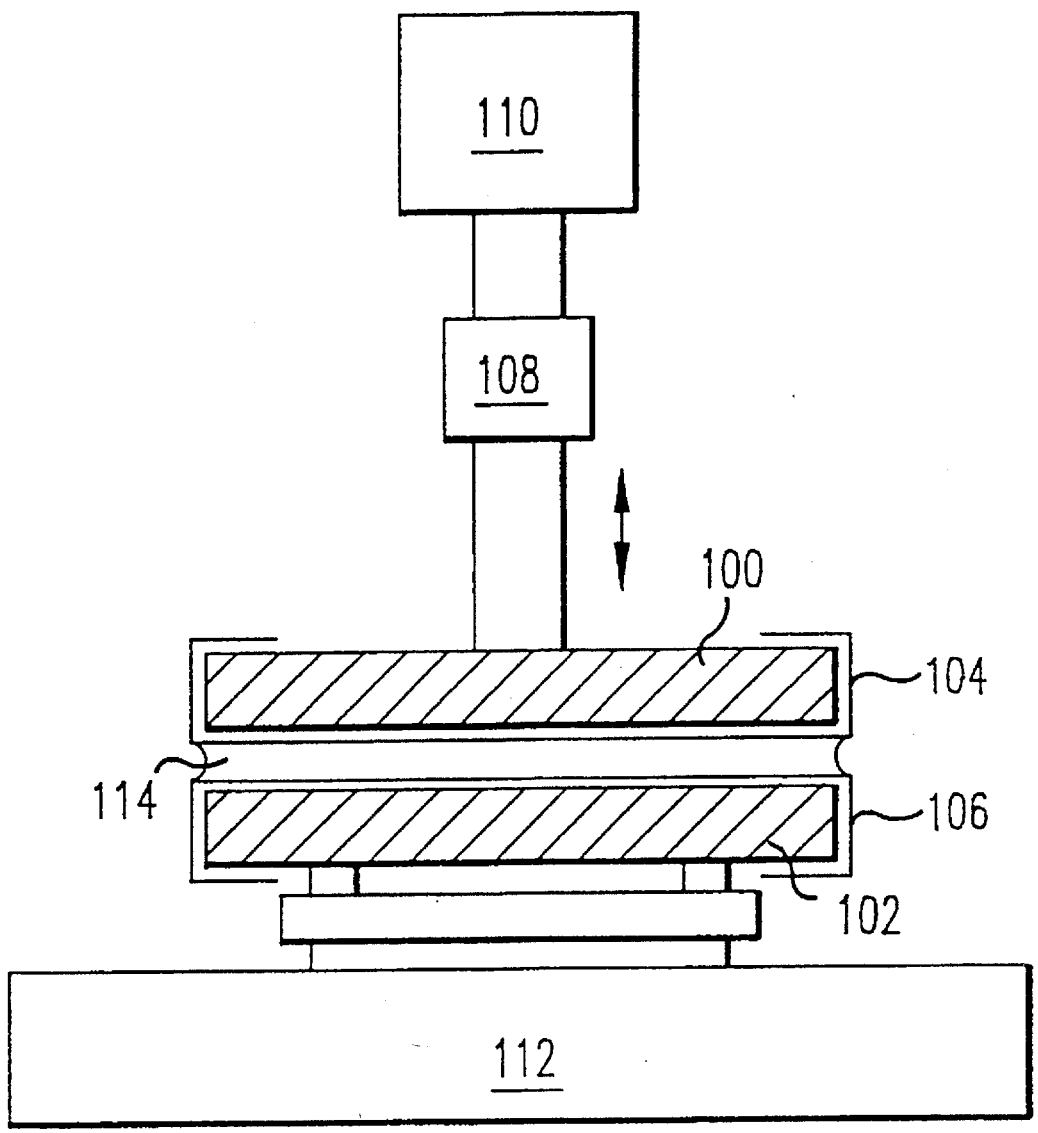
FIG. 7 is a schematic diagram of the apparatus used to determine average failure loads for various glove fluid layers.

FIG. 7 illustrates the apparatus used in the experiment. Two pieces of latex material 104 and 106 were glued onto the surface of two glass carriers 100 and 102, respectively. The pieces of latex were obtained from Travenol Triflex Sterile Latex Surgeons Gloves, size 8.5, in which powder had been removed by washing three times in 2 liters aqua bidest. The latex layers 104 and 106 were each 0.18 mm thick, while each glass carrier 100 and 102 was 6 mm thick.

Glass carrier 100 was mechanically connected to a micrometer 108 with 0.01 mm resolution. The glass carriers wee kept in substantially parallel alignment during movement. The micrometer 108 was driven by a stepping motor 110 at a rate of 1 mm/min.

Glass carrier 102 was pro-weighted with 300 g and connected to a rapidly indicating electronic balance 112. The contact area between the two carriers 100 and 102 was 2 in$^2$ (~25.81 cm$^2$).

Volumes ranging from 10 µl to 500 µl of colored bactericidal fluid 114, were pipetted onto the surface of carrier 102, and carrier 100 was lowered until the liquid 114 covered the entire contact area.

Carrier 100 was then lifted at a constant time rate by the stepper motor 110 via the micrometer 108. The maximum decrease in weight, indicated by the electronic balance 112, was reached shortly before rupture of the liquid layer 114 and noted.

Each experiment for a specific liquid volume was repeated seven times.

Figure 8:
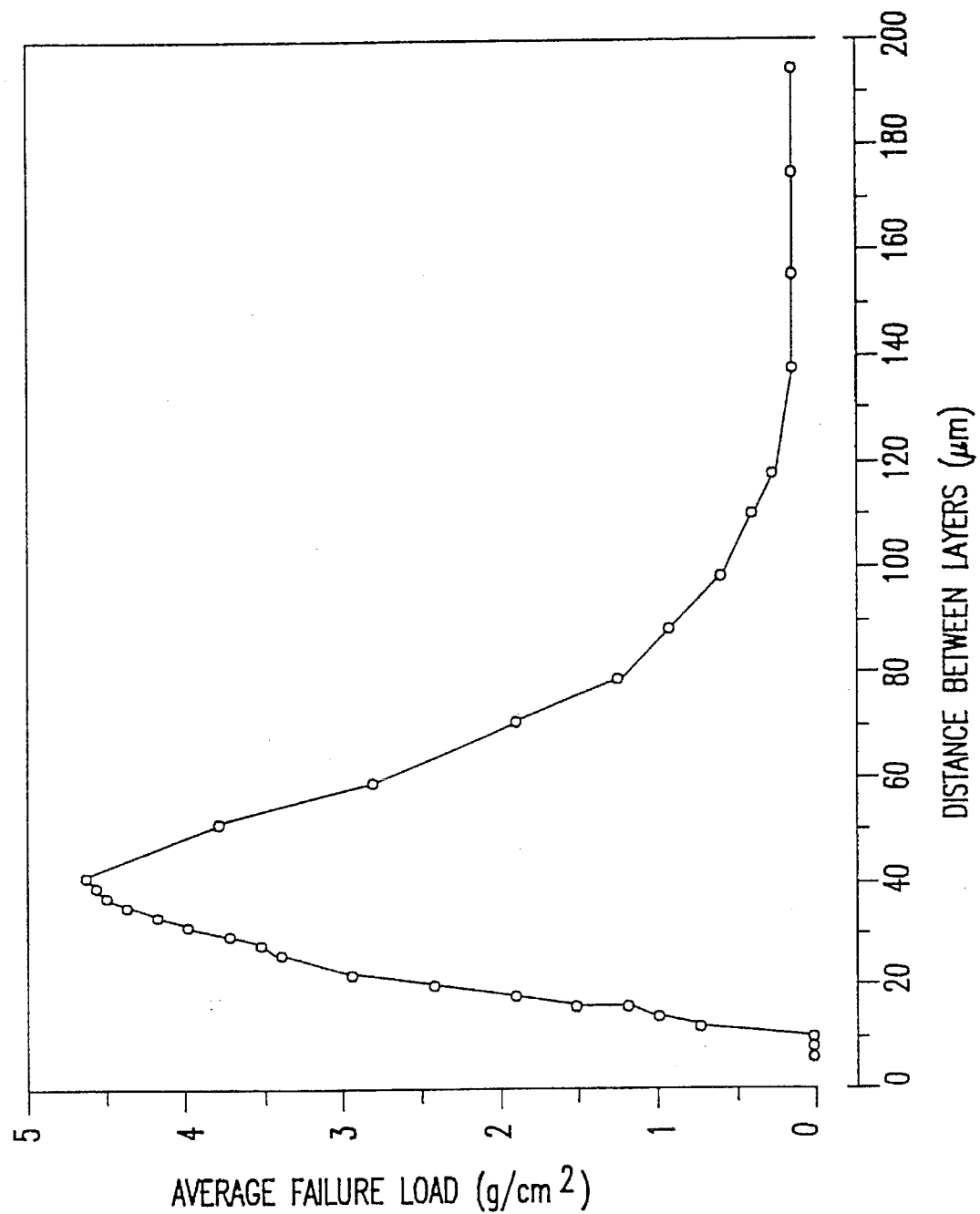
FIG. 8 is a plot of the experimental results of the average failure loads for various glove fluid layers.

The results of the experiment are shown in Table 1 and FIG. 8. The maximum AFL was reached at a liquid volume of around 100 µl (~0.039 mm fluid layer thickness). The AFL approached zero at volumes above 300 µl (~0.116 mm thick).

For comparison, the last column of Table 1 gives the required liquid volume, corresponding to the given liquid layer thickness, for a glove size 8.5 (surface area ~650 cm$^2$). Thus, for example, to obtain a fluid layer thickness of 0.039 mm between two size 8.5 gloves would require a fluid volume of about 2.518 ml.

TABLE 1

| LIQUID VOLUME (µl) | DISTANCE BETWEEN CARRIERS (LIQUID LAYER THICKNESS) (mm) | AVERAGE FAILURE LOAD (g/cm$^2$) | EQUIVALENT LIQUID VOLUME FOR GLOVE (ml/650 cm$^2$) |
|---|---|---|---|
| 10 | 0.004 | 0.000 | 0.252 |
| 15 | 0.006 | 0.000 | 0.378 |
| 20 | 0.008 | 0.000 | 0.504 |
| 25 | 0.010 | 0.697 | 0.630 |
| 30 | 0.012 | 0.969 | 0.756 |
| 35 | 0.014 | 1.124 | 0.881 |
| 40 | 0.015 | 1.434 | 1.007 |
| 45 | 0.017 | 1.860 | 1.133 |
| 50 | 0.019 | 2.402 | 1.259 |
| 55 | 0.021 | 2.867 | 1.385 |
| 60 | 0.023 | 3.371 | 1.511 |
| 65 | 0.025 | 3.487 | 1.637 |
| 70 | 0.027 | 3.681 | 1.763 |
| 75 | 0.029 | 3.952 | 1.889 |
| 80 | 0.031 | 4.184 | 2.015 |
| 85 | 0.033 | 4.339 | 2.141 |
| 90 | 0.035 | 4.456 | 2.267 |
| 95 | 0.037 | 4.494 | 2.392 |
| 100 | 0.039 | 4.611 | 2.518 |
| 125 | 0.048 | 3.719 | 3.148 |
| 150 | 0.058 | 2.751 | 3.778 |
| 175 | 0.068 | 1.860 | 4.407 |
| 200 | 0.077 | 1.162 | 5.037 |
| 225 | 0.087 | 0.814 | 5.666 |
| 250 | 0.097 | 0.504 | 6.296 |
| 275 | 0.107 | 0.310 | 6.926 |
| 300 | 0.116 | 0.116 | 7.555 |
| 350 | 0.136 | 0.000 | 8.814 |
| 400 | 0.155 | 0.000 | 10.074 |
| 450 | 0.174 | 0.000 | 11.333 |
| 500 | 0.194 | 0.000 | 12.592 |

The instant invention has been disclosed in connection with specific embodiments. However, it will be apparent to those skilled in the art that variations from the illustrated embodiments may be undertaken without departing the spirit and scope of the invention. For example, in connection with jobs where it is required that gloves be discarded after a certain amount of use, e.g. four hours, an absorption indicating substance might be placed between the glove layers to, e.g., change colors upon a certain degree of absorption.

I claim:

1. A glove comprising:

an inner layer;

an outer layer;

an impermeable seal between the inner and outer layers; and a middle layer comprising a sealing solution disposed between the inner and outer layers operable to seal holes in the inner or outer layers.

2. The glove of claim 1 wherein the sealing solution comprises a hydrogel.

3. The glove of claim 2 wherein the hydrogel is a natural hydrogel, a synthetic natural-based hydrogel, or a synthetic hydrogel.

4. The glove of claim 2 wherein the hydrogel is corn starch, potato starch, tapioca, sorghum starch, wheat starch, sago starch, or amylomaize starch.

5. The glove of claim 2 wherein the hydrogel is dextran, carboxymethylcellulose, methylcellulose, hydroxypropylmethylcellulose, or hydroxypropylcellulose.

6. The glove of claim 2 wherein the hydrogel is polyethylene glycol, polyethylene oxide, polyvinylpyrrolidone, hydroxyethyl methacrylate, polyhydroxyalkyl methacrylate or polymethacrylamide derivatives.

7. The glove of claim 1 wherein the sealing solution comprises corn starch.

8. The glove of claim 7 wherein the sealing solution comprises sucrose.

9. The glove of claim 7 wherein the sealing solution comprises nonoxynol-9.

10. The glove of claim 1 wherein the sealing solution comprises about 2–12 weight percent corn starch.

11. The glove of claim 1 wherein the sealing solution comprises about 4–10 weight percent corn starch.

12. The glove of claim 1 wherein the sealing solution comprises about 5–8 weight percent corn starch.

13. The glove of claim 1 wherein the sealing solution comprises potato starch.

14. The glove of claim 1 wherein the sealing solution comprises tapioca.

15. The glove of claim 1 wherein the sealing solution comprises an emulsifier.

16. The glove of claim 1 wherein the sealing solution comprises a surfactant.

17. The glove of claim 1 wherein the sealing solution comprises a dye.

18. The glove of claim 1 wherein the sealing solution comprises an antimicrobial solution.

19. The glove of claim 1 wherein the sealing solution comprises nonoxynol-9.

20. The glove of claim 1 wherein the sealing solution is operable to seal holes of up to about 0.15 mm average diameter.

21. The glove of claim 1 wherein the sealing solution is operable to seal holes of up to about 0.10 mm average diameter.

22. The glove of claim 1 wherein the sealing solution is operable to seal holes of up to about 0.07 mm average diameter.

23. The glove of claim 1 wherein the middle layer has an average thickness of less than about 0.12 millimeter.

24. The glove of claim 1 wherein the middle layer has an average thickness of between about 0.01 and 0.09 millimeter.

25. The glove of claim 1 wherein the middle layer has an average thickness of between about 0.025 and 0.05 millimeter.

26. The glove of claim 1 wherein the thickness of the glove is about 0.1 to 0.25 millimeter.

27. The glove of claim 1 wherein the first and second layers each have a thickness of between about 0.2 and 0.5 millimeters.

28. The glove of claim 2 wherein the hydrogel is operable to inhibit evaporation of the solution.

29. The glove of claim 1 wherein the glove maintains at least about 60 percent of its sealing solution when stored at 18°–21° C. and 50% relative humidity for 90 days.

30. The glove of claim 1 wherein the glove maintains about 10–60 percent of its sealing solution when stored at 18°–21° C. and 50% relative humidity for 90 days.

31. The glove of claim 1 wherein the glove maintains at least about 10 percent of its sealing solution when stored at 18°–21° C. and 50% relative humidity for 90 days.

32. The glove of claim 1 wherein the glove maintains at least about 75 percent of its sealing solution when stored at 18°–21° C. and 50% relative humidity for 21 days.

33. The glove of claim 1 wherein the glove maintains about 10–75 percent of its sealing solution when stored at 18°–21° C. and 50% relative humidity for 21 days.

34. The glove of claim 1 wherein the glove maintains at least about 10 percent of its sealing solution when stored at 18°–21° C. and 50% relative humidity for 21 days.

35. The glove of claim 1 which provides a sense of feel during use at least as great as the sense of feel of a single layer 0.200 mm thick latex glove.

36. The glove of claim 1 which provides a sense of feel during use at least as great as the sense of feel of a single layer 0.200 mm thick latex glove, but less than the sense of feel of a single layer 0.100 mm thick latex glove.

37. The glove of claim 1 wherein the sealing solution is operable to leak during use through holes in the inner layer and adhere the glove to a wearer.

38. A glove comprising:

an inner layer;

an outer layer;

an impermeable seal between the inner and outer layers; and a middle layer comprising an antimicrobial solution disposed between the inner and outer layers, said solution comprising an evaporation inhibitor operable to inhibit evaporation of the solution.

39. The glove of claim 38 wherein the antimicrobial solution comprises a hydrogel.

40. The glove of claim 39 wherein the hydrogel is a natural hydrogel, a synthetic natural-based hydrogel, or a synthetic hydrogel.

41. The glove of claim 38 wherein the antimicrobial solution comprises corn starch.

42. The glove of claim 38 wherein the glove maintains at least about 60 percent of its antimicrobial solution when stored at 18°–21° C. and 50% relative humidity for 90 days.

43. The glove of claim 38 wherein the glove maintains about 10–60 percent of its antimicrobial solution when stored at 18°–21° C. and 50% relative humidity for 90 days.

44. The glove of claim 38 wherein the glove maintains at least about 10 percent of its antimicrobial solution when stored at 18°–21° C. and 50% relative humidity for 90 days.

45. The glove of claim 38 wherein the glove maintains at least about 75 percent of its antimicrobial solution when stored at 18°–21° C. and 50% relative humidity for 21 days.

46. The glove of claim 38 wherein the glove maintains about 10–75 percent of its antimicrobial solution when stored at 18°–21° C. and 50% relative humidity for 21 days.

47. The glove of claim 38 wherein the glove maintains at least about 10 percent of its antimicrobial solution when stored at 18°–21° C. and 50% relative humidity for 21 days.

48. The glove of claim 38 which provides a sense of feel during use at least as great as the sense of feel of a single layer 0.200 mm thick latex glove.

49. The glove of claim 38 which provides a sense of feel during use at least as great as the sense of feel of a single layer 0.200 mm thick latex glove, but less than the sense of feel of a single layer 0.100 mm thick latex glove.

50. The glove of claim 38 wherein the antimicrobial solution is operable to leak during use through the gaps in the inner layer and adhere the glove to a wearer.

51. A condom comprising:

an inner layer;

an outer layer;

an impermeable seal between the inner and outer layers; and a middle layer comprising a sealing solution disposed between the inner and outer layers operable to seal holes in the inner or outer layers.

52. The condom of claim 51 wherein the sealing solution is operable to seal holes of up to about 0.15 mm average diameter.

53. The condom of claim 51 wherein the sealing solution is operable to seal holes of up to about 0.10 mm average diameter.

54. The condom of claim 51 wherein the sealing solution is operable to seal holes of up to about 0.07 mm average diameter.

55. The condom of claim 51 wherein the sealing solution comprises an antimicrobial solution.

56. The condom of claim 51 wherein the sealing solution comprises a hydrogel.

57. The condom of claim 56 wherein the hydrogel is a natural hydrogel, a synthetic natural-based hydrogel, or a synthetic hydrogel.

58. The condom of claim 51 wherein the sealing solution comprises corn starch.

59. The condom of claim 56 wherein the hydrogel is operable to inhibit evaporation of the solution.

60. The condom of claim 51 which maintains at least about 60 percent of its sealing solution when stored at 18°–21° C. and 50% relative humidity for 90 days.

61. The condom of claim 51 which maintains about 10–60 percent of its sealing solution when stored at 18°–21° C. and 50% relative humidity for 90 days.

62. The condom of claim 51 which maintains at least about 10 percent of its sealing solution when stored at 18°–21° C. and 50% relative humidity for 90 days.

63. The condom of claim 51 which maintains at least about 75 percent of its sealing solution when stored at 18°–21° C. and 50% relative humidity for 21 days.

64. The condom of claim 51 which maintains about 10–75 percent of its sealing solution when stored at 18°–21° C. and 50% relative humidity for 21 days.

65. The condom of claim 51 which maintains at least about 10 percent of its sealing solution when stored at 18°–21° C. and 50% relative humidity for 21 days.

66. The condom of claim 51 which provides a sense of feel during use at least as great as the sense of feel of a single layer 0.200 mm thick latex condom.

67. The condom of claim 51 which provides a sense of feel during use at least as great as the sense of feel of a single layer 0.200 mm thick latex condom, but less than the sense of feel of a single layer 0.100 mm thick latex condom.

68. The condom of claim 51 wherein the sealing solution is operable to leak during use through the gaps in the inner layer and adhere the condom to a wearer.

69. The condom of claim 51 wherein the sealing solution comprises a skin-adherent.

70. A condom comprising:

an inner layer;

an outer layer;

an impermeable seal between the inner and outer layers and a middle layer comprising an antimicrobial solution disposed between the inner and outer layers, said solution comprising an evaporation inhibitor operable to inhibit evaporation of the antimicrobial solution during use.

71. The condom of claim 70 wherein the antimicrobial solution comprises a hydrogel.

72. The condom of claim 71 wherein the hydrogel is a natural hydrogel, a synthetic natural-based hydrogel, or a synthetic hydrogel.

73. The condom of claim 70 wherein the antimicrobial solution comprises corn starch.

74. The condom of claim 70 wherein the antimicrobial solution is operable to adhere the first layer to the second layer.

75. The condom of claim 70 which maintains at least about 60 percent of its antimicrobial solution when stored at 18°–21° C. and 50% relative humidity for 90 days.

76. The condom of claim 70 which maintains about 10–60 percent of its antimicrobial solution when stored at 18°–21° C. and 50% relative humidity for 90 days.

77. The condom of claim 70 which maintains at least about 10 percent of its antimicrobial solution when stored at 18°–21° C. and 50% relative humidity for 90 days.

78. The condom of claim 70 which maintains at least about 75 percent of its antimicrobial solution when stored at 18°–21° C. and 50% relative humidity for 21 days.

79. The condom of claim 70 which maintains about 10–75 percent of its antimicrobial solution when stored at 18°–21° C. and 50% relative humidity for 21 days.

80. The condom of claim 70 which maintains at least about 10 percent of its antimicrobial solution when stored at 18°–21° C. and 50% relative humidity for 21 days.

81. The condom of claim 70 which provides a sense of feel during use at least as great as the sense of feel of a single layer 0.200 mm thick latex condom.

82. The condom of claim 70 which provides a sense of feel during use at least as great as the sense of feel of a single layer 0.200 mm thick latex condom, but less than the sense of feel of a single layer 0.100 mm thick latex condom.

83. The condom of claim 70 wherein the antimicrobial solution is operable to leak during use through the gaps in the inner layer and adhere the condom to a wearer.

84. A finger cot comprising:

an inner layer;

an outer layer;

an impermeable seal between the inner and outer layers; and middle layer comprising a sealing solution disposed between the inner and outer layers operable to seal holes in the inner or outer layers.

85. A finger cot comprising:

an inner layer;

an outer layer;

an impermeable seal between the inner and outer layers; and a middle layer of antimicrobial solution disposed between the inner and outer layers, said solution comprising an evaporation inhibitor operable to inhibit evaporation of the antimicrobial solution during use.

* * * * *

UNITED STATES PATENT AND TRADEMARK OFFICE
CERTIFICATE OF CORRECTION

PATENT NO. : 5,483,697
DATED : January 16, 1996
INVENTOR(S) : Ingbert E. Fuchs

It is certified that error appears in the above-indentified patent and that said Letters Patent is hereby corrected as shown below:

```
In claim 84, column 22, line 42, delete "middle" and insert
therefor --a middle--.
```

Signed and Sealed this

Thirtieth Day of April, 1996

Attest:

BRUCE LEHMAN

*Attesting Officer*          *Commissioner of Patents and Trademarks*